United States Patent [19]

Maynard

[11] 4,308,873
[45] Jan. 5, 1982

[54] ELECTROENCEPHALOGRAPH MONITORING

[75] Inventor: Douglas E. Maynard, London, England

[73] Assignee: National Research Development Corporation, London, England

[21] Appl. No.: 18,894

[22] Filed: Mar. 9, 1979

[30] Foreign Application Priority Data

Mar. 16, 1978 [GB] United Kingdom ............... 10382/78
Oct. 10, 1978 [GB] United Kingdom ............... 40034/78

[51] Int. Cl.³ .............................................. A61B 5/04
[52] U.S. Cl. .................................. 128/731; 128/642; 128/643
[58] Field of Search ............................ 128/639–644, 128/710–712, 731–734, 748, 902, 901

[56] References Cited

U.S. PATENT DOCUMENTS

| | | | |
|---|---|---|---|
| 3,599,628 | 8/1971 | Abbenante et al. | 128/748 X |
| 3,699,947 | 10/1972 | Maynard | 128/731 |
| 3,732,859 | 5/1973 | Tateno | 128/731 |
| 3,826,243 | 7/1974 | Anderson | 128/732 |
| 3,945,374 | 3/1976 | McClure | 128/733 |
| 3,951,136 | 4/1976 | Wall | 128/642 |
| 3,957,036 | 5/1976 | Normann | 128/642 |
| 4,084,583 | 4/1978 | Hjort | 128/731 |

OTHER PUBLICATIONS

Rosen et al., "The Human Fetal Electroencephalogram", Am. J. Ob. & Gyn., 1969, vol. 104, pp. 1057–1060.
Chacheva, "Fetal EEG", 5th Eur. Cong. of Perinatal Med., Jun., 1976, pp. 116–119.
Zorn et al., "Electroencephalographic Foetele", J. Obs. & Gyn., Biol. Repr., 1974, 3, 1035–1055.
Rosen et al., "Human Fetal Electroencephalogram", Obs. & Gyn., 1976, vol. 36, pp. 132–139.
Mann et al., "Human Fetal . . . Electrode", Am. J. Obs. & Gyn., 1972, vol. 114, pp. 893–903.
Rosen et al., "An Approach to Study of Brain Damage", Am. J. Ob. & Gyn., 1973, vol. 115, pp. 37–47.
Peltzman et al., "Quan. Analysis of Fetal . . . Data", Am. J. Ob. & Gyn., 1973, vol. 115, pp. 1117–1124.

Primary Examiner—Lee S. Cohen
Attorney, Agent, or Firm—Cushman, Darby & Cushman

[57] ABSTRACT

Apparatus for monitoring those signals in the brain which give rise to electroencephalograms (EEG) is described. The apparatus is particularly applicable to the fetus where EEG signals often contain a component of those signals which give rise to electrocardiographs (ECG). In the apparatus ECG signals picked up by electrodes in an electrode assembly forming part of the apparatus are eliminated by deriving two signals having equal ECG components, the two signals being subtracted from one another to provide a signal representing EEG. The electrodes may be concentric annular electrodes, for example, or relatively small disc electrodes spaced apart at the vertices of an equilateral triangle.

12 Claims, 12 Drawing Figures

ELECTROENCEPHALOGRAPH MONITORING

This invention relates to improvements in or relating to the monitoring of those electrical signals from the brain which on display on a chart recorder provide recordings known as electroencephalograms (EEG). For this reason in this specification and claims "EEG" refers to these electrical signals in the brain. The invention is more particularly concerned with apparatus for monitoring the EEG of a human fetus, but may also find application in the determination of death of the brain, for example following cardiac arrest.

The monitoring of EEG of a fetus, during labour of the mother, can assist in identifying the effects on the fetus of anaesthetic and other drugs administered to the mother. Furthermore a major cause of concern during labour is the maintenance of adequate fetal blood circulation, particularly to the fetal brain. At present an estimate of the state of the fetal brain is inferred indirectly from:

(a) the fetal electrocardiograph, normally in the form of a display of fetal heart rate (FHR), where various patterns of FHR alteration with maternal contractions are assigned particular significance.

(b) analysis of fetal scalp venous blood samples.

Existing techniques suffer from the disadvantage that estimates of the state of the fetal brain are performed indirectly. It would be advantageous to measure the fetal brain state by more direct means. This has been done by recording of the fetal electroencephalogram. However this is an unwieldy technique with considerable technical problems and is unlikely to be used other than for research. For example the technique monitors the EEG signals from a fetus by applying to its scalp a pair of electrodes, each having a sharp single pointed contact, held in place to the scalp by a suction cup. This has the disadvantage that pressure applied to the outside of the cup, for example by the mother's uterus wall, may transmit varying high pressures to the area of the scalp under the contact surface of the electrodes. This is known to produce large fluctuating voltage potentials at the contact areas, which are thought to result in part from alterations of local blood flow.

A further major disadvantage of this arrangement is that an electrical signal recorded between such pair of electrodes may frequently contain those electrical signals which on display on a chart recorder provide recordings known as electrocardiographs. In this specification and claims "ECG" refers to electrical signals in the body due to activity of the heart. Thus the desired EEG signal from the fetus usually contains an ECG component.

A further disadvantage arises in monitoring fetal EEG signals (FEEG) because an electroencephalograph recorder produces a paper trace at the rate of 108 meters per hour, whereas FHR recording may be carried out at paper speeds of the order of 30 to 60 cm per hour.

An object of the present invention is to provide an improved apparatus for monitoring EEG.

According to the present invention there is provided apparatus for monitoring EEG comprising a plurality of electrodes, an insulated casing in which the electrodes are mounted and which is constructed to be held to the scalp of the brain to be monitored, and an electrical circuit, including amplification means connected to the electrodes, at least the said circuit being arranged to minimise the effect of ECG, picked up by way of the electrodes, on the output signal of the circuit.

The amplification means may comprise a differential amplifier.

The electrodes may comprise a first circular electrode (preferably of annular plan section), and a second annular electrode concentrically mounted within the first electrode.

In another arrangement the electrodes may comprise at least three discrete electrodes preferably spaced from each other by equal distances, said electrodes being connected to the amplification means.

The resulting electrical signals from the three said electrodes may be combined in any proportion by a potential divider means either before or after aplification.

Where there are three electrodes, the potential divider means may be a two-gang potentiometer, one section of which may alternatively be connected by switching means to any two electrodes and the other section of which is connected to the third electrode to provide a path having an impedance between the scalp and the amplifier equal to the total impedance of the parallel paths by way of the other two electrodes between the scalp and the amplifier, the variable tappings of the two sections of the potentiometer being fed to a differential amplifier. In this manner adjustments of the potentiometer in conjunction with the switching means may be used to cancel out the ECG signal.

The contact surface of each of the discrete electrodes may be planar, but roughened to provide a large surface area. Preferably, however, the contact surface is of a conical or domed form, also with surface roughening, thus further increasing the contact area.

The insulated casing, in which the electrodes are mounted, preferably fully surrounds each electrode except for its contact surface.

The apparatus may further include a slow speed chart recorder and means for providing signals to the recorder so that at least some of, and preferably all, the following traces are drawn by the recorder:- FHR, maternal contractions and/or intrauterine pressure, FEEG, impedance between the said electrodes and the scalp, and muscle activity. A number of slow speed chart recorders could of course be used in place of one such recorder.

The ECG and hence FHR may be derived from signals from a further electrode fixed to the insulated casing and contractions and intrauterine pressure may be sensed by a strain gauge on the casing or a pressure transducer associated with the casing.

Certain embodiments of the invention will now be described, by way of example only, with reference to the accompanying drawings, in which.

Figure 1:
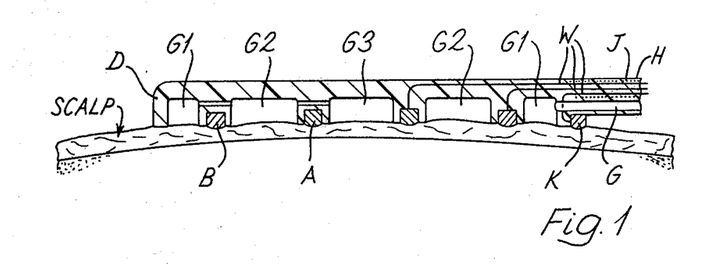
FIG. 1 is an enlarged view in section of a first electrode assembly used in apparatus according to the invention, shown applied to the scalp of the brain of a fetus to be monitored.
Figure 2:
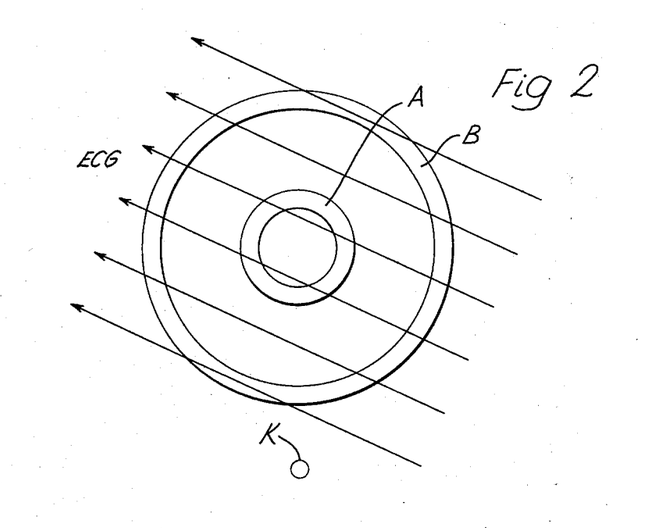
FIG. 2 is an enlarged plan view of the individual electrodes of FIG. 1.

With reference first to FIGS. 1 and 2, an inner ring A is shown concentrically mounted within an outer ring B. Each ring is made of electrically conductive material. (The inner ring A may alternatively be a circular disc.) The direction of the ECG current flow, which varies but may be assumed to flow approximately parallel to the scalp surface, is shown by a series of parallel lines ECG (FIG. 2). This current flow produces a potential gradient across the fetal scalp which is also conducted to the rings A and B.

If there is no contact resistance between the outer ring B and the scalp, the current will flow around ring B instead of through the resistive medium of the scalp. This results in an equipotential field around the inner ring A which, via the resistive medium of the scalp, attains the same potential as outer ring B. Thus no potential difference arising from the ECG occurs between the rings.

If, as is more likely, there is a contact impedance between the scalp and the rings A and B, then ECG currents, from points of contact along the potential gradient on the scalp, will pass to the rings from these points. Thus each ring will tend to attain a potential which is an average of the potential gradient under it. Consequently the potential attained by the outer ring B will be the same as that attained by the inner concentric ring A, assuming that there is uniform electrical contact and that the potential gradient is linear as it passes under the rings.

In contrast, although the EEG scalp potential may show potential gradients across the scalp which could be cancelled in a manner similar to that of the ECG, these potentials also occur with local maxima and minima which may change position from moment to moment. Such potential fields will frequently produce potential differences between rings A and B. The potential differences may then be amplified by electronic means.

Referring again to FIG. 1, the concentric rings A and B are preferably made of silver with a silver chloride coating, but may be made of any suitable conductive material. The rings are set in a casing D of insulating material which may, for example be silicone rubber or plastic. The insulating material surrounds the entire rings apart from the contact surface adjacent the scalp. The casing D may for example be typically about 25 mm in diameter.

The electrode is held to the scalp by means of light suction (of the order of 80 cm of water) which is applied via a tube G to an annular void G1 outside the ring B. The annular void G1 is connected in turn to an annular void G2 and to a cylindrical void G3 inside the ring A. The voids serve to increase the area to which suction is applied and to draw the skin of the fetal scalp around the rings to improve the seal therewith, thus avoiding fluid matter being drawn in from around the scalp.

In use on the fetal scalp, the electrode assembly is placed on the scalp while in the uterus when the cervix has dilated to about 2 cms.

The rings A and B are connected to insulated leads W which form the inner conductors of an electrical cable H, screened by a screen J and incorporating the suction tube G.

For the purposes of electrical amplification, the leads W are connected to a differential amplifier. A suitable amplifier for this purpose is that disclosed in United States Reissue Patent No. 28,214. The screen J of the cable H may be connected to an electrical screen containing the amplifier and/or to a reference potential. A further non-insulated electrode K is mounted on the outside of the casing D to record ECG potentials.

It will be seen that this electrode assembly has a large area of contact with the scalp, so that varying pressures applied to the cup (for example by the uterus wall of the mother) are not localised. Further reduction of potential fluctuations, induced for example by contractions of the mother, may be achieved by keeping the overall height of the casing D above the scalp to a minimum, as shown in FIG. 1.

Figure 3:
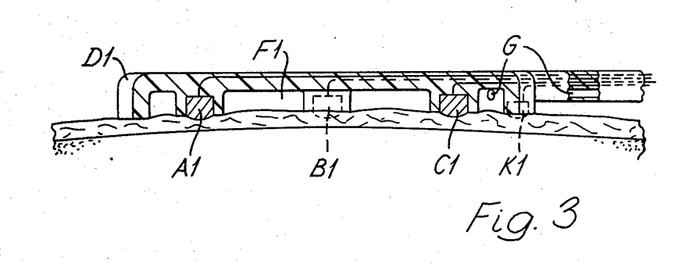
FIG. 3 is an enlarged view in section of a second electrode assembly used in apparatus according to the invention.
Figure 4:
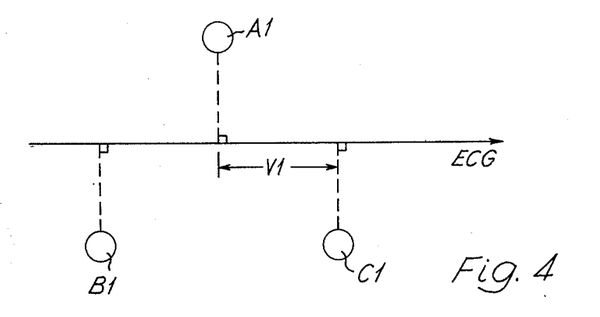
FIG. 4 is an enlarged plan view of some of the individual electrodes of FIG. 3.

In an alternative electrode assembly, shown in section in FIG. 3, there are provided three electrodes A1, B1 and C1 spaced at equal distances from one another in the form of an equilateral triangle (see FIG. 4). The arrowed line ECG represents the direction at a particular instant of the scalp surface current flow from the ECG. This current flow produces a potential gradient across the scalp. Assuming this gradient to be linear, the contribution of the ECG to the voltage recorded between any pair of the electrodes is proportional to the length between the perpendicular projections of the pair of electrodes on to the line ECG; for example, between electrodes A1 and C1 the contribution of voltage is V1 (FIG. 4). Thus the ECG potential at electrode A1 lies between that at electrodes B1 and C1, and by tapping the voltage between B1 and C1 by means of a potential divider (as to be described below), an ECG potential can be derived which is the same as that at electrode A1. By feeding this derived potential and that at electrode A1 to a differential amplifier which subtracts the two potentials, the resulting signal contains no contribution from ECG.

Although at any moment the EEG scalp potential may have a potential gradient, the direction of this changes from moment to moment and thus the electrical energy is not cancelled in the same way as that from the ECG.

Referring again to FIG. 3 the electrodes A1, B1 and C1 are mounted in an insulated casing D1. Outside the casing is mounted a further electrode K1 which (as previous electrode K) may be used in conjunction with any one of the electrodes A1, B1 or C1 to give a signal indicative of the ECG of the body being monitored.

The casing D1 surrounds each of the three electrodes locally, leaving a void space F1 to which suction is applied by a suction tube which is similar to that one described with reference to FIG. 1. The contact surfaces of each of the three electrodes are of a domed form, but roughened to provide a large surface area.

A simple circuit for using the method described above is shown in FIG. 5. A switch SW is a three pole 3-way switch by means of which any of the signals from electrodes A1, B1 or C1 may be selected. RV1 is a two-gang potential divider, incorporating two potentiometers RV1a and RV1b each of 50 Kohm.

Figure 5:
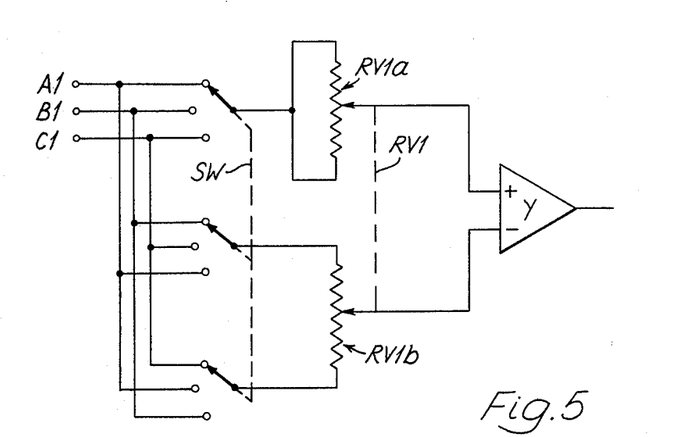
FIG. 5 is a control circuit for use with the second electrode assembly.

In the position of the switch SW shown in FIG. 5, the signal from electrode A1 is fed to RV1a, while those from electrodes B1 and C1 are fed to RV1b. Thus RV1b taps the ECG potential across the electrodes B1 and C1, and RV1a provides an equal impedance path in the lead from the electrode A1. The equal impedance path is important because the common mode rejection characteristics of differential amplifiers, such as amplifier Y shown in FIG. 5, are impaired by unequal impedances in their input leads. The amplifier Y is used to subtract the two signals from the potential divider RV1 and to give an output voltage which may be observed on an oscilloscope or chart recorder. RV1 is then adjusted until the ECG contribution as shown on the oscilloscope or chart recorder disappears from the signal. If the direction of the ECG signal (FIG. 4) is such that the largest potential difference occurs between electrodes A1 and B1, for example, instead of B1 and C1, then it is necessary to alter the position of the switch SW by trial and error to achieve the desired cancellation of the ECG.

Adjustment of the potentiometer RV1 and perhaps a new position for the switch SW are needed each time the fetal head changes position in relation to the fetal heart since ECG currents then change direction.

In practice the introduction of impedance in the input leads to the amplifier Y may worsen its susceptibility to electrical interference to such an extent that an unsatisfactory signal is produced. It may then be necessary to provide three differential amplifiers one for each of the outputs between pairs of electrodes A1 B1, B1 C1, and C1 A1.

Figure 6:
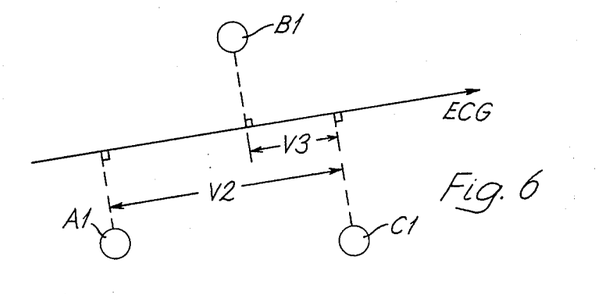
FIG. 6 is an enlarged plan view similar to FIG. 4.

Referring now to FIG. 6, V3 is shown as the amplified ECG voltage across electrodes B1 and C1, and V2 that across electrodes C1 and A1. It will be seen that V2 may be divided in a similar manner to that shown with reference to FIGS. 4 and 5, until a result equal to V3 is obtained. The two signals may then be applied to a final differential amplifier to remove the ECG signal, as previously.

In practice it may not be convenient to use the manual arrangements of the switch SW and potential divider RV1 of FIG. 5 to perform the adjustments necessary for removal of the ECG signal. However there are many alternative control arrangements in the present state of electronic art by which such adjustments may be performed both manually and automatically, and one automatic arrangement is now described.

Figures 7A, 7B:
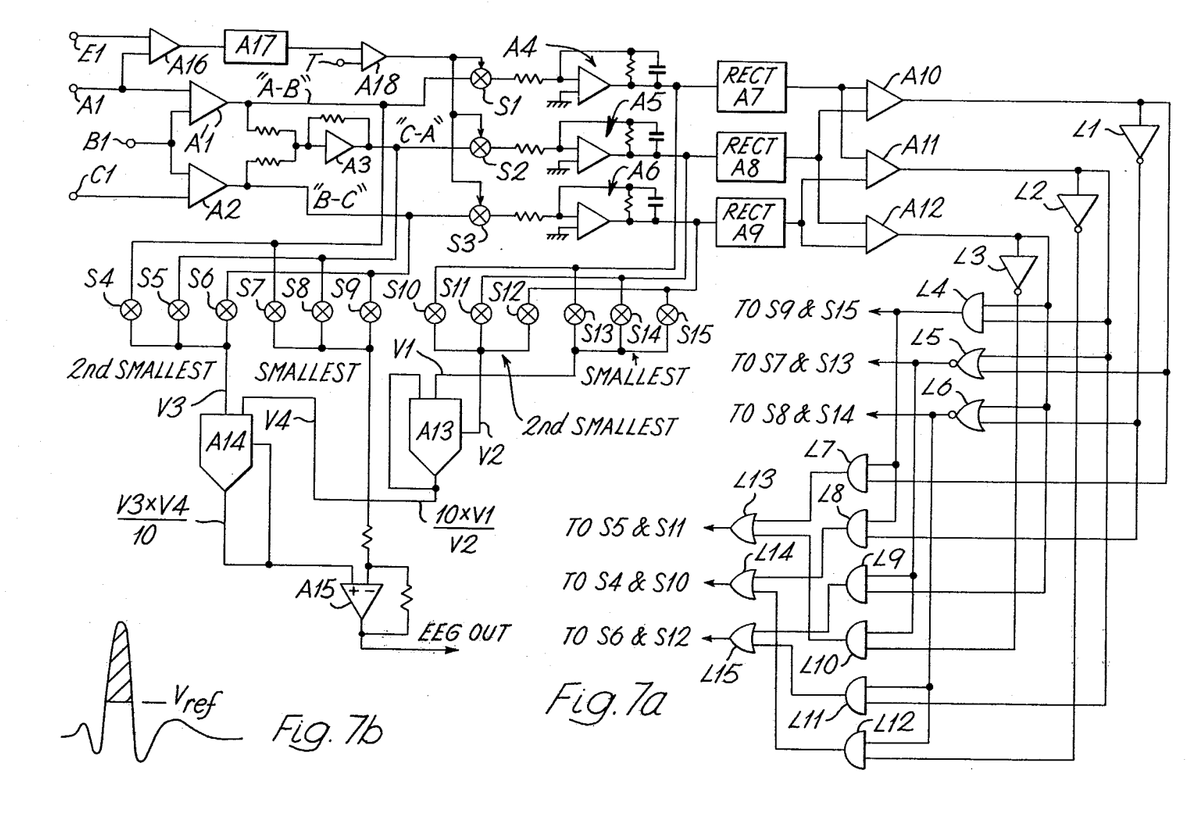
FIG. 7a is a block diagram of an arrangement for use with three electrodes for substantially eliminating the ECG component.
FIG. 7b shows the ECG waveform which occurs intermittently once each time the heart beats.

The arrangement shown in FIG. 7a provides automatic removal of ECG signals from EEG signals. The three electrodes A1, B1 and C1 are connected to two differential isolation amplifiers A'1 and A2 to provide difference signals "A-B" (that is signals having instantaneous values equal to the voltage appearing on the electrode A1 minus that on the electrode B1) and "B-C", and the outputs of amplifiers A'1 and A2 are connected by way of resistors to a differential circuit including an operational amplifier A3 connected to have a gain of one and to provide an output "C-A". Amplifiers A'1, A2 and A3 are connected by way of switches S1, S2 and S3 to "leaky" integrators A4, A5 and A6, respectively, which may alternatively be considered as low pass filters. These switches are controlled by the ECG waveform as follows: the output from an isolation amplifier A16 coupled to electrodes E1 and A1 (see FIGS. 8a and 8b described below) has an intermittent output ECG waveform approximately as shown in FIG. 7b, this waveform occurring for a relatively short interval each time a fetal heartbeat occurs. An automatic gain control amplifier A17 couples the output of the amplifier A16 to a comparator A18 so that the positive extremes of the waveform of FIG. 7b are always the same after processing by the amplifier A17, as are the negative extremes, although positive and negative extremes are not, in general, equal. A reference voltage $V_{ref}$ indicated in FIG. 7b is applied to a terminal T so that the comparator A18 opens the switches S1, S2 and S3 only when the shaded part of the ECG waveform occurs. Thus the integrators A4, A5 and A6 receive signals only during the shaded portion of the ECG.

Amplifiers A1, A2 and A16 may be type IA 296 manufactured by INTRONICS of 57 Chapel Street, Newton, Mass. 02155, U.S.A.

Output signals from the integrators are rectified by full-wave rectifier circuits A7, A8 and A9 which may be constructed for example as described in "Linear Applications" published in 1973 by National Semiconductors, Volume 1, pages AN31-12. The rectified signals are applied to comparators A10, A11 and A12 which provide binary "one" signals if $K(A-B) > K(C-A)$, $K(A-B) > K(B-C)$ and $K(C-A) > K(B-C)$, respectively; where $K(A-B)$ is the long-term ECG component of "A-B" and $K(B-C)$ and $K(C-A)$ have similar meanings. The comparators A10, A11, A12 and A18 may be National Semiconductors type LM 139.

Application of the signals from comparators A10, A11 and A12 to a logic circuit comprising invertors L1, L2 and L3 (such as type 7404), a positive AND gate L4, and positive NOR gates L5 and L6 (such as type 7402) provide control signals for pairs of switches S9 and S15, S7 and S13, and S8 and 14, respectively. The signals at the outputs of the gates L4, L5 and L6 each become a binary "one" when the ECG components of the signals "A-B", "B-C" and "C-A", hereinafter referred to as the said three signals, is smallest.

Positive AND gates L7 to L12 and positive OR gates L13, L14 and L15 (such as type 7432) connected as shown in FIG. 7a provide control signals for pairs of switches S5 and S11, S4 and S10, and S6 and S12 when the second smallest ECG component in the said three signals occurs in "C-A", "A-B" and "B-C", respectively. The positive AND gates mentioned above may be type 7408.

A divider circuit A13, which may be a 4-quadrant multiplier/divider such as INTRONICS type M530 connected as a divider, forms a signal representing the ratio of the smallest ECG component derived from the said three signals divided by the second smallest component. Thus the output signal from the divider A13 represents a ratio which when used to multiply that one of the said three signals with the second smallest long term ECG component, produces a signal having the same long term ECG component as the signal having the smallest component. The input signals for the divider A13 are supplied by way of the switches S10 to S15 under the control of the outputs of the gates L4, L5 and L6 and the gates L13, L14 and L15.

The output signal from the divider circuit A13 is applied as one input to a multiplier circuit A14 which again may be INTRONICS type M530 but connected as a multiplier. The other input signal for the multiplier A14 is that one of the said three signals with the second smallest long-term ECG component and is applied by way of the switches S4, S5 and S6 controlled by the gates L13, L14 and L15. The multiplier 14 provides an output signal representing the second smallest of the said three signals multiplied by the output of the divider A13, that is a signal in which the long-term ECG component is equal to the long-term ECG component in that signal having the smallest such component.

Finally, that signal with the smallest long-term ECG component is applied by way of the switches S7, S8 and S9 controlled by the gates L4, L5 and L6 to an operational amplifier A15 connected to subtract two input signals. The amplifier A15 also receives the output signal from the multiplier A14 as an input signal so its input signals contain equal ECG components and thus its output is an EEG signal free of such components.

The circuit of FIG. 7a can, of course, be modified in many ways and in particular the signals representative of long-term ECG components may be derived from the outputs of the amplifiers A'1, A2 and A3 by multipliers which multiply each amplifier output signal by the ECG signal from the amplifier A16 or A17. The product signals so formed are then passed to a square root circuit before integration by the integrators A4, A5 and A6.

In an alternative arrangement the outputs from the amplifiers A'1, A2 and A3 are passed to respective analogue-to-digital converters coupled to a microprocessor. A program of the microprocessor selects the digital samples of the two signals with the lowest and second lowest ECG component and adjusts one of these samples so that the ECG components of the two samples are equal, one sample then being subtracted from the other to give an EEG signal sample free of ECG. Samples of all three of the signals A-B, B-C and C-A are multiplied by samples of the ECG signal and the results are averaged, preferably by the known technique of exponentially backwards weighting in order to determine which signals have the smallest and second smallest long-term ECG component. Additionally, the microprocessor may be programmed to carry out the difference operations carried out by the amplifiers A'1.

As has been mentioned the provision of a number of simultaneous traces showing various measured values is useful in interpreting EEG waveforms. An embodiment of the invention for this purpose is now described with reference to FIGS. 8a and 8b.

Figure 8A:
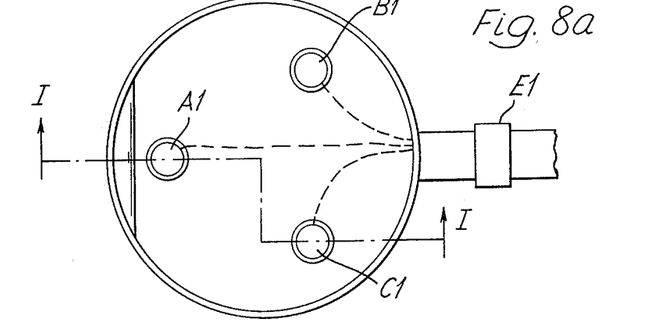
FIG. 8a is a view from underneath a three electrode assembly.
Figure 8B:
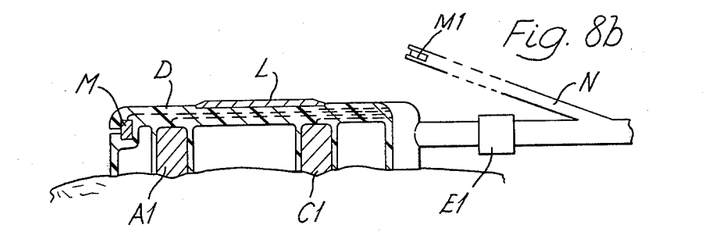
FIG. 8b is a cross section on the line I—I of FIG. 8a with the electrode B1 omitted for clarity.

A tripolar electrode of the same general type as is shown in FIG. 3 has three electrodes A1, B1 and C1 contained within an electrically insulated cup D which is applied to the fetal head by means of a light suction applied by a vacuum line G. An electrode E1 external to the cup, but in contact with the uterine environment will, when a recording is taken differentially between it and any one of the electrodes within the cup, record the FECG. A pressure transducer L is mounted on the cup in such a position that it will measure the pressure applied to the electrode assembly by the uterine wall. The transducer may be of any suitable sort, such as a strain gauge.

A further pressure transducer M may be mounted in such a manner that its pressure registering surface is protected from the uterine wall so that it measures the pressure applied to it by the intrauterine fluids. Alternatively a substitute M1 for the transducer M may be on a flexible extension N from the electrode so that it measures the pressure in a region more remote from the fetal head. Thus although both M and M1 are shown in FIG. 8b, in practice either one or the other would usually be present.

Amplifiers (not shown) may be contained either within the cup assembly or in a separate assembly close to the electrode assembly. The purpose of such amplifiers is to avoid or minimise the recording of electrical interference which may occur, typically but not exclusively, capacitively, inductively, or mechanically as a result of movements of electrode leads.

Once the FECG has been removed, the FEEG may be processed by first filtering using a band pass filter. The filter heavily attenuates low frequencies which may contain artefactual electrical activity not of FEEG origin. The frequency at which such attenuation may begin may be adjustable or fixed, but will typically be in the range of 0.5 to 3 Hz. The filter attenuates frequency activity above an upper limit. In particular it will reject frequencies which originate from the main electricity supply (50 or 60 Hz). The upper limit may be variable or fixed but will typically be within the range 15 to 40 Hz.

A filter of the sort described in U.K. Pat. No. 1247491 and U.S. Pat. No. Re. 28214 is suitable but other filters with the above mentioned general characteristics may be used.

The filtered FEEG activity is then subjected to logarithmic amplitude compression by passing it through a logarithmic amplifier. After amplitude compression the signal is detected and the result smoothed to give a varying output proportional to the amplitude variations of the envelope of the amplitude compressed FEEG signal. The processing may thus be substantially as described in the above mentioned patents but as an alternative amplitude compression may be carried out after detection. The smoothed output is applied to a recording pen which, as the chart paper moves slowly under it, moves to and fro to write a thick band on the chart (see P in FIG. 9).

Means Q (see FIG. 10) for monitoring the electrical impedance between the recording electrodes may also be provided in order to ensure that the electrodes A1, B1 and C1 are in contact with the fetal scalp. An alternating current is applied across the electrodes from a high resistance source. The voltage developed across the electrodes is proportional to, and indicates, the impedance between the electrodes. The frequency of the alternating current is above that of the FEEG frequencies to be recorded. For a trielectrode assembly the alternating current may be applied at two different frequencies to two pairs of the three electrodes to enable simultaneous measurement of the impedances between each pair. More conveniently, a time division multiplexed alternating signal is applied first to one electrode pair and then another and so on.

This facility may be extended to the external FECG recording electrode and to the pressure measuring devices to ensure their continuity and to give warning of failure.

Figure 10:
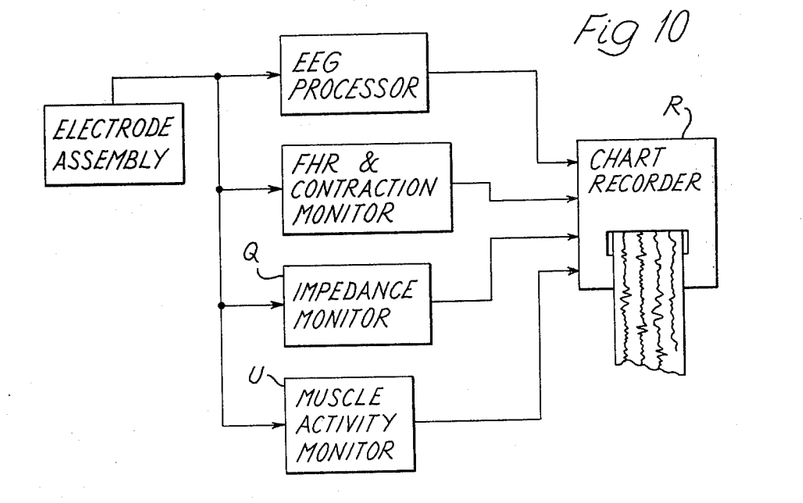
FIG. 10 is a block diagram showing circuits in block form for supplying a chart recorder from an electrode assembly of the type shown in FIG. 3 or FIG. 8a (Note the connections shown in FIG. 10 are mainly multiple conductor connections).

The amplified impedance signal is detected and an output provided to a channel of a chart recorder R which indicates the state of the electrodes. For example a pen deflection proportional to total impedance measurement may be obtained, or means of indicating the impedances of each separate electrode separately may be provided.

Electrical activity originating in the uterine environment and believed to be due to muscle activity may also be usefully monitored, using a monitor U, and shown as a recorder trace. The signal may be obtained either from the FEEG electrodes A1, B1 and C1 where signals due to muscle activity, either of fetal or maternal origin, that may be contaminating the FEEG is of interest; or from the FECG electrode K1 and one of the FEEG electrodes. A pair of electrodes external to the electrode assembly, and specially situated to record electrical activity in the uterine environment may be used. After application, the muscle signal is band pass filtered using filters situated in one or other of two frequency ranges: the first filter range is selected to be above that of the FEEG frequencies of interest, but below the frequency of the main electricity supply (50/60 Hz); and the second frequency range begins above double the mains supply frequency (100/120 Hz) and may continue to some upper limit of the order of 1 KHz. The upper frequency range is preferred, but there may be occasions when harmonic distortion components of the mains supply, or rectifier ripple, may extend into this frequency range and cause a false indication of the level of muscle activity. In such circumstances the filter situated below the mains frequency may be used. This has the disadvantage that some FEEG activity may occur in this frequency range.

Since muscle activity contains energy covering a wide frequency range which may include that of the FEEG, it is important to know when it is present, so that false FEEG readings can be identified. Once band pass filtered, the muscle activity is processed in the same manner as the FEEG.

An alternative embodiment of the band pass filter used for the muscle activity signals covers a frequency range from above the selected FEEG frequency range to some upper limit which may be of the order of 100 Hz to 1 KHz and which includes frequencies of mains origin. However these latter frequencies are stopped by a comb filter which is connected to attenuate mains frequencies and their harmonics to a level where they are of no significance. Such a filter may be locked to the mains frequency; but is however arranged with the stop bands extending over a range on either side of the harmonically distributed frequencies. The purpose is to remove or greatly attenuate those side band frequencies that may be caused by amplitude modulation of the interfering signal of mains origin.

An example of traces obtained from a chart recorder supplied with the signals mentioned above is shown in FIG. 9.

Figure 9:
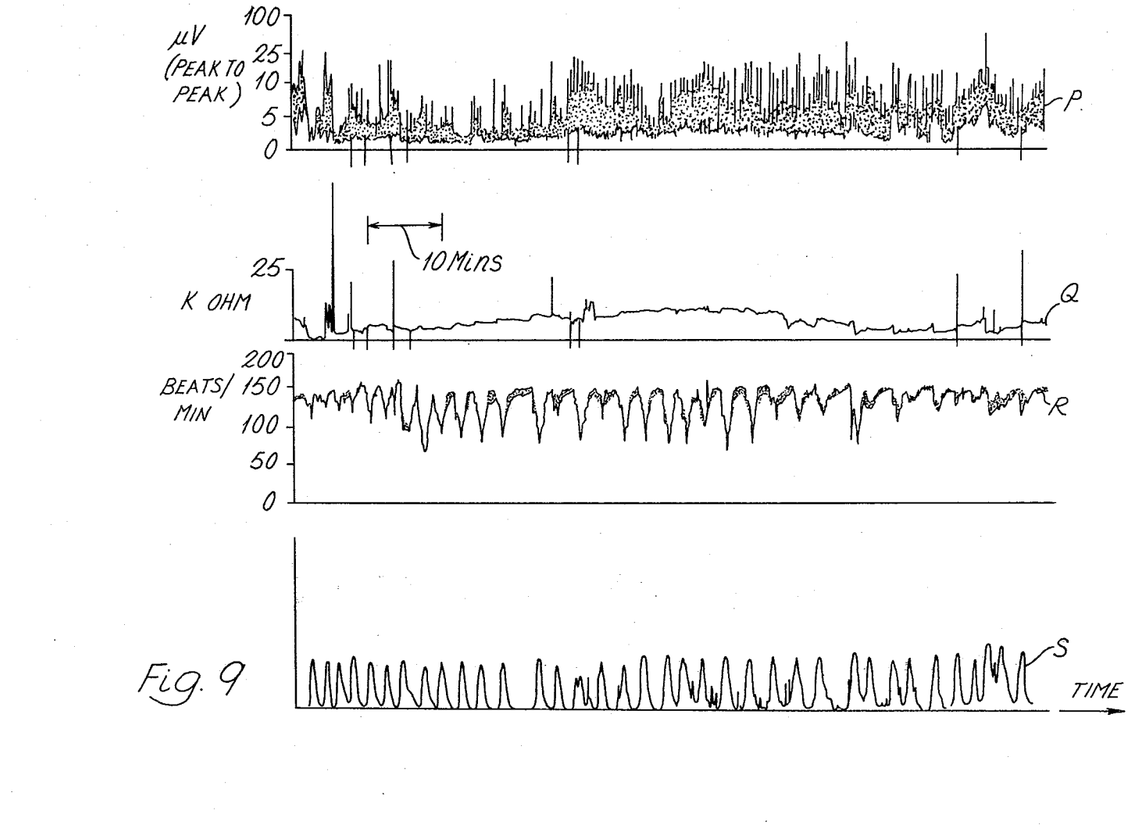
FIG. 9 illustrates traces produced by a slow-speed chart recorder from apparatus according to an embodiment of the invention.

The top trace P represents the fluctuation of amplitude of the processed FEEG signal. The second trace Q shows variations of the impedance between the FEEG recording electrodes. The third trace R shows the variations of FHR in beats/minute. The lower trace S shows the timing of maternal contractions.

At the beginning of the trace the FEEG shows a drop to a lower level before the onset of FHR dips to a lower rate. After about 35 minutes there is a change of character of the FEEG trace. When the FHR dips decrease in magnitude there is a brief castellated appearance in the FEEG trace followed by a rise to a higher level.

I claim:

1. Apparatus for monitoring a brain electroencephalogram (EEG) comprising:
   at least three electrodes providing voltage signals indicative of brain EEG,
   an insulated carrier on which the electrodes are mounted and which is constructed to be held to the scalp of the brain to be monitored,
   first circuit means for providing a first signal which is a function of the voltage signals at two of the electrodes,
   second circuit means for providing a second signal which is, at least partially, a function of the voltage signal at a third of the electrodes,
   adjustment means capable of so adjusting at least one of the first and second signals so that any electrocardiograph (ECG) components of the first and second signals become equal to one another, and
   difference means for deriving an output signal representative of the difference between the first and second signals after the adjustment by the adjustment means.

2. Apparatus according to claim 1 wherein the electrodes are spaced from each other by equal distances.

3. Apparatus according to claim 1 wherein the first circuit means comprises switching means for selecting signals from two of the three electrodes, and wherein the adjustment means is capable of deriving any voltage between the voltages of the selected electrodes, and wherein the second circuit means supplies, in operation the voltage of the electrode which has not been selected by the switching means to the difference means.

4. Apparatus according to claim 3 wherein the difference means comprises a differential amplifier and the adjustment means comprises a two-gang potentiometer, one section of which may alternatively be connected by the switching means to any two electrodes and the other section of which is connected to the third electrode to provide a path having an impedance between the scalp and the amplifier equal to the total impedance of the parallel paths by way of the other two electrodes between the scalp and the amplifier, the variable tappings of the two sections of the potentiometer being connected to the inputs of the differential amplifier.

5. Apparatus according to claim 1 wherein the first and second circuit means each comprise a further difference means for deriving signals representative of the difference between voltages of a first and second of the electrodes and the first and a third of the electrodes, respectively, the adjustment means being capable of so adjusting the output of at least one of the further difference means that two signals having equal ECG components are provided for use in deriving the output signal.

6. Apparatus according to claim 5, wherein the adjustment means is automatic, the apparatus including long term ECG monitoring means for deriving monitor signals representative of the voltage component due to ECG over a plurality of intervals of ECG signals in the outputs of at least both of said further difference means, and control means for controlling the adjustment means in accordance with the output of the monitoring means.

7. Apparatus according to claim 6 wherein said long term ECG monitoring means comprises:
   electrode means for sensing an ECG signal;
   ECG amplifier means for amplifying said ECG signal;
   comparator means for comparing an amplified ECG signal from said ECG amplifier means with a reference signal and generating a comparator signal each time the amplified ECG signal exceeds the reference signal;
   switch means associated with each of said further difference means for selectively passing signals therefrom, each switch means being operated to pass its associated signal when the comparator signal is applied to a control input thereof;

integrator means associated with each such switch means for receiving a signal from its associated further difference means and passed by its associated switch means;

logic circuit means, responsive to each said integrator means for controlling the processing of signals from said further difference means, thereby providing automatic adjustment of the levels thereof.

8. Apparatus according to claim 1 comprising three further difference means, each for deriving a respective one of the three differences between the voltages of the three electrodes, and wherein the first circuit means comprises selection means for selecting the further difference means output signal in which the ECG component has a value between the ECG components in the two other further difference means output signals for application, as the first signal, to the adjustment means, and wherein the second circuit means comprises further selection means for selecting the further difference means output signal having the lowest ECG component as the said second signal.

9. Apparatus according to claim 1 including monitor means for deriving at least one of the following signals: heart rate, maternal contractions, intrauterine pressure, impedance between the electrodes and the scalp, and muscle activity; and a slow-speed chart recorder connected to the difference means to display said output signal and connected to the monitor means to display signals therefrom.

10. Apparatus according to claim 1 wherein the insulated carrier is resilient and defines a void adjacent to the electrodes, and a tube connected to the void is provided for connecting the void to a low pressure source to allow suction to be applied to the void to hold the insulated carrier to the scalp.

11. Apparatus according to claim 1 including a pressure transducer fixed to the insulated carrier.

12. Apparatus for monitoring a brain electroencephalogram (EEG) comprising:

at least three electrodes, an insulated carrier on which the electrodes are mounted and which is constructed to be held to the scalp of the brain to be monitored, and means for (a) deriving a first difference signal from the voltages on a first and a second of the electrodes, (b) deriving a second difference signal from the voltages on the second electrode and a third of the electrodes, (c) automatically providing respective signals, from the first and second difference signals, which have substantially equal components due to an electrocardiograph (ECG), and (d) subtracting one of the signals having an ECG component from the other such signal.

* * * * *